United States Patent

Abrecht

Patent Number: 6,114,541
Date of Patent: *Sep. 5, 2000

[54] METHOD FOR THE PREPARATION OF α-BROMO-LACTAM DERIVATIVES

[75] Inventor: Stefan Abrecht, Duggingen, Switzerland

[73] Assignee: Hoffmann-La Roche Inc., Nutley, N.J.

[*] Notice: This patent issued on a continued prosecution application filed under 37 CFR 1.53(d), and is subject to the twenty year patent term provisions of 35 U.S.C. 154(a)(2).

[21] Appl. No.: 09/019,941

[22] Filed: Feb. 6, 1998

[30] Foreign Application Priority Data

Mar. 10, 1997 [EP] European Pat. Off. .............. 97103964

[51] Int. Cl.$^7$ .................................................. C07D 207/12
[52] U.S. Cl. ................................................................ 548/543
[58] Field of Search ................................................ 548/543

[56] References Cited

U.S. PATENT DOCUMENTS 5,523,400 6/1996 Wei et al. ................................ 514/202

FOREIGN PATENT DOCUMENTS 620 225 A1 3/1994 European Pat. Off. .
97/26260 7/1997 WIPO .

OTHER PUBLICATIONS

Happ, David N. et al., An Efficient alpha–Halogenation of Acyl Chlorides . . . , J. Org. Chem., 40 (23), Dec. 1975.
Okawara, Tadashi et al., Synthesis of New Uraciles . . . , Heterocycles, 27 (8), Dec. 1988.
Tadashi Okawara, Toshifumi Shono, Tesuo Yamasaki, & Mitsuru Furukawa, Synthesis of New uraciles having N–Amino–β–γ–, and β–lactams, Heterocycles, 27, 1988, 1881–1885.
Clayton H. Heathcock, John C. Kath, & Roger B. Ruggeri, Daphniphyllum Alkaloids. 16. Total Synthesis of (+)–Codaphniphylline, J. Org. Chem., 60, 1995, 1120–1130.
Harpp, David N., et al., J. Org. Chem., 40(23):3420–3427 (1975).
Ikuta, H., et al., J. Med. Chem., 30:1995–1998 (1987).

Primary Examiner—Johann Richter
Assistant Examiner—Dominic Keating
Attorney, Agent, or Firm—George W. Johnston; Patricia S. Rocha-Tramaloni; Eileen M. Ebel

[57] ABSTRACT

The invention is concerned with a new process for the preparation of compounds of formula

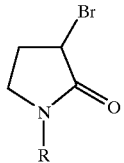

I wherein
R is hydrogen, lower alkyl, lower alkoxy, cycloalkyl, cycloalkenyl, cycloalkyl-lower alkyl, lower alkenyl, lower alkynyl, aryl, aryl-lower alkyl, heterocyclyl or heterocyclyl-lower alkyl; the lower alkyl, cycloalkyl, lower alkenyl, cycloalkenyl, lower alkynyl, aryl-lower alkyl, aryl and the heterocyclyl moieties being unsubstituted or substituted with at least one group selected from carboxy, amino, carbamoyl, nitro, cyano, lower alkyl, lower alkoxy, hydroxy, halogen, aminomethyl, mercapto, trifluoromethyl and trichloroethyl.

The compounds prepared according to above mentioned process are useful in the preparation of cephem, isoxacephem and carbacephem derivatives.

17 Claims, No Drawings

METHOD FOR THE PREPARATION OF α-BROMO-LACTAM DERIVATIVES

The present invention is related to a new method for the preparation of compounds of formula

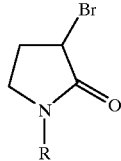

I wherein
R is hydrogen, lower alkyl, lower alkoxy, cycloalkyl, cycloalkenyl, cycloalkyl-lower alkyl, lower alkenyl, lower alkynyl, aryl, aryl-lower alkyl, heterocyclyl or heterocyclyl-lower alkyl; the lower alkyl, cycloalkyl, lower alkenyl, cycloalkenyl, lower alkynyl, aryl-lower alkyl, aryl and the heterocyclyl moieties being unsubstituted or substituted with at least one group selected from carboxy, amino, carbamoyl, nitro, cyano, lower alkyl, lower alkoxy, hydroxy, halogen, aminomethyl, mercapto, trifluoromethyl, and trichloroethyl.

Compounds of formula I are known compounds. They are used for making cephem derivatives as described in EP-A 620 225 (U.S. Pat. No. 5,523,400), carbacephem derivatives as described in EP appl. no. 97116236.7 or isoxacephem derivatives as described in WO 97/26260. In a known process these lactam derivatives are prepared starting with butyrolactone which is opened and brominated in the presence of elemental bromine and phosphortribromide to form dibromobutyric acid which is reacted with thionylchloride. The resulting 2,4-dibromo-butyric acid chloride is amidated and then transformed to the compound of formula I. This method is characterized by poor yields of the desired product and undesirable reagents as elemental bromine and phosphortribromide.

Thus, an object of the present invention is to provide a more economical and higher yielding process, and other advantages as discussed below, over the known process.

As used herein, the term "lower alkyl" refers to both straight and branched chain saturated hydrocarbon groups having 1 to 8, preferably 1 to 4 carbon atoms, for example, methyl, ethyl, n-propyl, isopropyl, tertiary butyl and the like. The lower alkyl groups can be unsubstituted or substituted by at least one substituent as mentioned above. Preferred substituents include fluoro, examples of substituted lower alkyl are trifluoromethyl, trifluoroethyl, perfluorohexyl and the like.

By term "lower alkoxy" is meant an ether group wherein alkyl is as defined above. Examples are methoxy, ethoxy, propyloxy and the like.

By the term "cycloalkyl" is meant a 3 to 7 membered saturated carbocyclic ring e.g., cyclopropyl, cyclobutyl, cyclopentyl, cyclohexyl and the like. "Cycloalkyl-lower alkyl" is an alkyl group as defined above with an attached cycloalkyl ring, preferred cycloalkyl-lower alkyl are for example cyclopropylmethyl or cyclopropylethyl. By the term "cycloalkenyl" is meant a 4–7 membered carbocyclic ring having at least one olefinic double bond, e.g. cyclopentenyl.

As used herein, "lower alkenyl" refers to an unsubstituted or substituted hydrocarbon chain radical having from 2 to 8 carbon atoms, preferably from 2 to 4 carbon atoms, and living at least one olefinic double bond, e.g. vinyl, allyl, and the like.

As used herein, "lower alkynyl" refers to an unsubstituted or substituted hydrocarbon chain radical having from 2 to 8 carbon atoms, preferably 2 to 4 carbon atoms, and having at least one triple bond.

The term "halogen" used herein refers to chlorine or chloro; bromine or bromo; iodine or iodo; and fluorine or fluoro.

By the term "aryl" is meant a radical derived from an aromatic hydrocarbon by the elimination of one atom of hydrogen and can be substituted or unsubstituted. The aromatic hydrocarbon can be mononuclear or polynuclear. Examples of aryl radicals of the mononuclear type include phenyl, tolyl, xylyl, mesityl, cumenyl, and the like. Examples of aryl radicals of the polynuclear type include naphthyl, anthryl, phenanthryl, and the like. The aryl group can have at least one substituent selected from halogen, hydroxy, cyano, carboxy, carbamoyl, nitro, amino, aminomethyl, lower alkyl, lower alkoxy, mercapto, trichloroethyl or trifluoromethyl. Examples include 2-fluorophenyl, 3-nitrophenyl, 4-nitrophenyl, 4-methoxyphenyl, 4-hydroxyphenyl, and the like.

By the term "aryl-lower alkyl" is meant a lower alkyl group containing an aryl group as defined above, for example benzyl.

As used herein, "heterocyclyl" refers to an unsaturated or saturated, unsubstituted or substituted 5-, 6-, or 7-membered heterocyclic ring containing at least one hetero atom selected from the group consisting of oxygen, nitrogen, or sulfur. Exemplary heterocyclic rings include, but are not limited to, e.g., the following groups: pyrrolidinyl, pyridyl, pyridiniumyl, pyrazinyl, piperidyl, piperidino, N-oxido-pyridyl, pyrimidyl, piperazinyl, pyrrolidinyl, pyridazinyl, N-oxide-pyridazinyl, pyrazolyl, triazinyl, imidazolyl, thiazolyl, 1,2,3-thiadiazolyl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl, 1,2,3-triazolyl, 1,2,4-triazolyl, 1H-tetrazolyl, 2H-tetrazolyl, thienyl, azetidinyl, furyl, hexamethylene-iminyl, oxepanyl, 1H-azepinyl, thiophenyl, tetrahydrothiophenyl, 3H-1,2,3-oxathiazolyl, 1,2,3-oxadiazolyl, 1,2,5-oxadithiolyl, isoxazolyl, isothiazolyl, 4H-1,2,4-oxadiazinyl, 1,2,5-oxathiazinyl, 1,2,3,5-oxathiadiazinyl, 1,3,4-thiadiazepinyl, 1,2,5,6-oxatriazepinyl, oxazolidinyl, tetrahydrothienyl, and the like. Preferred heterocyclic rings are pyridyl, pyridiniumyl, piperidyl, pyrrolidinyl and azetinyl. Substituents for the heterocyclic ring include lower alkyl, lower alkoxy, halogen, trifluoromethyl, trichloroethyl, amino, mercapto, hydroxy, aminomethyl, nitro, cyano, carboxy or carbamoyl. Preferred examples of substituted heterocyclic rings include 5-methyl-isoxazol-3-yl, N-methyl-pyridinium-2-yl, N-methyl-pyrrolidinyl, 1-methyl-tetrazolyl and N-aryl-carbamoyl, methyl-pyridinium-2-yl.

The heterocyclic ring can also be substituted by an optionally substituted phenyl ring such as 2,6-dichlorophenyl. Preferred is 2,6-dichlorophenyl-5-methyl-isoxazolyl. A further substituent of the heterocyclic ring is oxo, such as in 2-oxo-oxazolidin-3-yl, 1,1-dioxo-tetrahydrothien-3-yl. The heterocyclic ring can also be fused together with a benzene ring.

As used herein, "heterocyclyl-lower alkyl" refers to a lower alkyl group containing a heterocyclic group as defined above, e.g. tetrazolyl-methyl, tetrahydrofuranyl-methyl, thiophenyl-methyl or benzimidazolyl-methyl.

It has been found that compounds of formula I can be made in an improved and more economic manner by the two step method according to the invention, which comprises
  a) reacting 4-chloro-butyric acid chloride (1) with N-bromosuccinimide in an inert solvent by adding first thionylchloride, immediately followed by a catalytic amount of hydrobromic acid to form a compound of formula

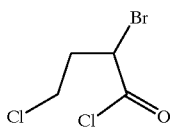

(2)

b) and reacting the compound (2) with an amine of formula

R—NH$_2$ (3)

wherein R is as defined above
in a non-aqueous medium in presence of sodium or potassium hydroxide and a phase transfer catalyst according to the reaction Scheme 1 depicted below to yield the desired compound of formula I in high yields.

Scheme 1

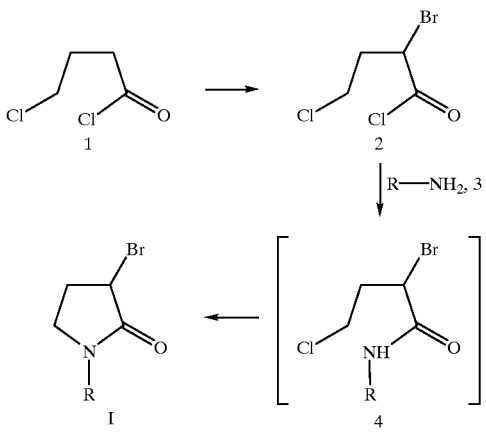

wherein R is as defined above. The compound of formula 1 is then conveniently separated from the reaction mixture.

The bromination of 4-chloro-butyric acid chloride (1) proceeds smoothly and without the formation of by-products when the reaction is carried out in an inert solvent, preferably a chlorinated hydrocarbon as for example dichloromethane, tetrachloromethane and the like, by suspending the acid chloride (1) and the N-bromo-succinimide in a ratio 1 to 1.5 molar and subsequently adding from about 5 to about 10 mol % thionylchloride, such as from 5 to 10 mol % thionylchloride, preferably 5 mol %, immediately followed by a catalytic amount, preferably 3 mol % with respect to the acid chloride, of hydrobromic acid. The brominated acid chloride (2) is then—without any further purification—reacted with a R-substituted amine (3) to form the amide (4) which is cyclized in situ to yield the compound of formula I.

According to the invention the formation of the amide (4) and the cyclization reaction are carried out in a single step by suspending sodium or potassium hydroxide, preferably as anhydrous pearls, together with a phase transfer catalyst in a non-aqueous medium and adding under vigorous stirring the R-substituted amine (3) followed by a solution containing the brominated acid chloride (2). During the addition of (2) the reaction temperature raises and is then maintained at about 40° C. to 45° C. during the reaction.

The method according to the invention improves the preparation of compounds of formula I by shortening the process, by obtaining higher yields, and by avoiding problematic reagents, as elemental bromine and by decreasing the production costs.

Compounds of formula I prepared according to the invention can be used for making cephem, carbacephem and isoxacephem derivatives of formula

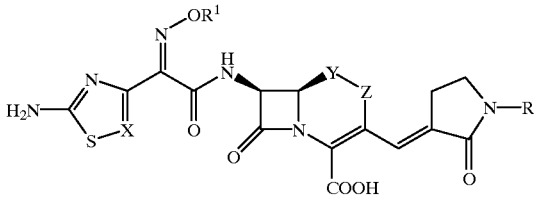

II wherein
R$^1$ is hydrogen, lower alkyl which is unsubstituted or substituted by one or more groups selected from halogen, hydroxy, cyano, nitro, carboxy and carbamoyl, cycloalkyl, aryl lower alkyl trityl, acetyl or tetrahydropyranyl;
R is as defined above;
Y is -S- and Z is -CH$_2$- or
Y is -CH$_2$- and Z is -O-, or
Y and Z each are -CH$_2$-; and
X is -CH- or nitrogen.

The following examples illustrate the invention in more detail and are not intended to be a limitation in any manner.

EXAMPLE 1

Procedure for the Preparation of 2-Bromo-4-chlorobutyric Acid Chloride

In a 1.5-liter 4-necked flask, equipped with a stirrer, reflux condenser, thermometer and argon inlet, 280.0 g 4-chlorobutyric acid chloride (1.98 mol) and 546.0 g N-bromosuccinimide (3.06 mol) were suspended with stirring, under argon in 560 ml dichloromethane; 12.0 g thionylchloride (0.10 mol) were added to the mixture, immediately followed by 3.60 ml 48% hydrobromic acid. The initially yellowish solution turned dark orange. The reaction mixture was refluxed during 1.5 h. The red-brown solution was evaporated. The resulting orange residue (800.7 g) was dispersed in 1.40 l n-hexane during 5 minutes, filtered under argon and the residue washed with n-hexane. The combined filtrates were evaporated to yield 352 g of 2-bromo-4-chloro-butyric acid chloride as yellowish oil. This product could be used in further steps without purification.

EXAMPLE 2

2. 1. Procedure for the Preparation of N-Cyclopropylmethyl-3-bromopyrrolidine-2-one In a 1.5-liter 4-necked flask, equipped with a stirrer, dropping funnel, reflux condenser, thermometer and argon inlet, 54.4 g sodium hydroxide pearls (1.36 mol) and 9.26 g tetrabutylammonium hydrogensulfate (27.3 mmol) were suspended with stirring at room temperature under argon in 500 ml dichloromethane. To the suspension 35.6 g aminomethylcyclopropane (500 mmol) were added. A solution of 100.0 g 2-bromo-4-chlorobutyric acid chloride (400 mmol, product of Example 1) in 100 ml dichloromethane was added during 10 min. After the first 3 min. of addition, reflux was reached and maintained during the addition. After completed addition, the mixture was refluxed for 1 h, during which its color changed from dark green to dark brown. The suspension was cooled to room temperature during 10 min., and a mixture of 50 g ice and 250 ml deionized water was added under stirring. The phases were separated and the organic layer was successively washed with a solution of 60 g ammonium chloride in 300 ml deionized water, followed by 300 ml deionized water. The organic layer was concentrated to yield 94.2 g of N-cyclopropylmethyl-3-bromopyrrolidine-2-one as a dark oil.

2.2. Procedure for the Preparation of N-isobutyl-3-bromopyrrolidine-2-one

In a 1.5-liter 4-necked flask, equipped with a stirrer, reflux condenser, thermometer and argon inlet, 54.4 g NaOH pearls (1.36 mol) and 9.26 g tetrabutylammonium-hydrogensulfate (27.3 mmol) were suspended at room temperature under argon in 500 ml dichloromethane. To this suspension 36.6 g isobutylamine (500 mol) were added. Under stirring 100.0 g 2-bromo-4-chlorobutyric acid chloride (400 mol, product of Example 1) in 100 ml dichloromethane were added in 10 min. After the first three minutes of addition reflux of the mixture was reached and maintained during the addition. Reflux of the mixture was continued for 2.0 h. After the first 10 minutes, the initially yellowish suspension turned purple, then gradually faded into gray. After completed reflux, the mixture was allowed to cool to room temperature during 15 min., a mixture of 50 g ice in 250 ml deionized water was added under stirring during 1 min., and the phases were separated. The organic phase was first washed with a solution of 60 g ammonium chloride in 300 ml deionized water, then with 300 ml deionized water, and finally evaporated to yield 84.3 g of N-isobutyl-3-bromopyrrolidine-2-one as a dark oil.

2.3. Procedure for the Preparation of N-Cyclopropyl-3-bromopyrrolidin-2-one

N-cyclopropyl-3-bromopyrrolidin-2-one was prepared in analogy to the procedure described in Examples 2.1. and 2.2. using cyclopropylamine instead of methylcyclopropane and isobutylamin, respectively.

I claim:

1. A process for making a compound of formula

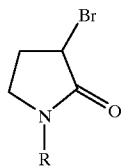

(I)

wherein

R is hydrogen, lower alkyl, lower alkoxy, cycloalkyl, cycloalkenyl, cycloalkyl-lower alkyl, lower alkenyl, lower alkynyl, aryl, aryl-lower alkyl, heterocyclyl or heterocyclyl-lower alkyl; the lower alkyl, cycloalkyl, lower alkenyl, cycloalkenyl, lower alkynyl, aryl-lower alkyl, aryl and the heterocyclyl moieties being unsubstituted or substituted with at least one group selected from carboxy, amino, amido, carbomoyl, nitro, cyano, lower alkyl, lower alkoxy, hydroxy, halogen, aminomethyl, mercapto, trifluoromethyl, and trichloroethyl, comprising the steps of a) reacting 4-chloro-butyric acid chloride with N-bromosuccinimide in an inert solvent by adding first from about 5 to about 10 mol % thionylchloride, immediately followed by a catalytic amount of hydrobromic acid to form a compound of formula

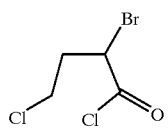

(2)

b) reacting the compound (2) with an amine of formula

R—NH$_2$ (3)

wherein R is as defined above in a non-aqueous medium in presence of sodium or potassium hydroxide and a phase transfer catalyst to form the compound of formula I, and c) separating the compound of formula I from the reaction mixture.

2. The process of claim 1, wherein the 4-chloro-butyric acid chloride and N-bromosuccinamide are present in a ratio from about 1 to about 1.5 molar.

3. The process of claim 1, wherein the thionylchloride is present in an amount of about 5 mol percent.

4. The process of claim 3, wherein the hydrobromic acid is present in an amount of about 3 mol percent.

5. The process of claim 1, wherein the inert solvent is a chlorinated hydrocarbon.

6. The process of claim 5, wherein the chlorinated hydrocarbon is selected from dichloromethane and tetrachloromethane.

7. The process of claim 1 wherein the sodium or potassium hydroxide is present in form of anhydrous pearls.

8. The process of claim 1, wherein R is lower alkyl, cycloalkyl, cycloalkyl-alkyl, or heterocyclyl; the lower alkyl being unsubstituted or substituted by at least one halogen.

9. The process of claim 8, wherein the lower alkyl is unsubstituted.

10. The process of claim 9, wherein the lower alkyl is isobutyl.

11. The process of claim 8, wherein the lower alkyl is substituted by at least one halogen.

12. The process of claim 11, wherein the lower alkyl is trifluoroethyl.

13. The process of claim 8, wherein the cycloalkyl is cyclopropyl.

14. The process of claim 8, wherein the cycloalkyl-alkyl is cyclopropylmethyl.

15. The process of claim 8, wherein the heterocyclyl is pyrrolidin.

16. The process of claim 1, wherein the thionylchloride is present in an amount of from 5 to 10 mol %.

17. The process of claim 16, wherein the thionylchloride is present in an amount of 5 mol %.

* * * * *